(12) United States Patent
Bagaoisan et al.

(10) Patent No.: US 10,470,750 B2
(45) Date of Patent: *Nov. 12, 2019

(54) LAPAROSCOPIC FASCIAL CLOSURE SYSTEM

(71) Applicant: TELEFLEX MEDICAL INCORPORATED, Morrisville, NC (US)

(72) Inventors: Celso Bagaoisan, Union City, CA (US); Suresh Pai, Los Altos, CA (US); Brad Labarbera, Ludlow, KY (US)

(73) Assignee: Teleflex Medical Incorporated, Morrisville, NC (US)

( * ) Notice: Subject to any disclaimer, the term of this patent is extended or adjusted under 35 U.S.C. 154(b) by 363 days.

This patent is subject to a terminal disclaimer.

(21) Appl. No.: 15/401,173

(22) Filed: Jan. 9, 2017

(65) Prior Publication Data

US 2017/0112481 A1   Apr. 27, 2017

Related U.S. Application Data

(63) Continuation of application No. 14/564,331, filed on Dec. 9, 2014, now Pat. No. 9,539,002.

(60) Provisional application No. 61/913,910, filed on Dec. 9, 2013.

(51) Int. Cl.
| | |
|---|---|
| *A61B 17/00* | (2006.01) |
| *A61B 17/04* | (2006.01) |
| *A61B 17/06* | (2006.01) |
| *A61B 90/00* | (2016.01) |

(52) U.S. Cl.
CPC ...... *A61B 17/0057* (2013.01); *A61B 17/0469* (2013.01); *A61B 17/0482* (2013.01); *A61B 17/0485* (2013.01); *A61B 17/0491* (2013.01); *A61B 17/0493* (2013.01); *A61B 2017/00637* (2013.01); *A61B 2017/00663* (2013.01); *A61B 2017/06042* (2013.01); *A61B 2090/036* (2016.02)

(58) Field of Classification Search
CPC ............ A61B 17/0469; A61B 17/0057; A61B 17/0482; A61B 2017/00663; A61B 17/0493; A61B 2017/0472; A61B 2017/06042; A61B 17/0483; A61B 17/0485; A61B 2017/00349
USPC ................................ 606/139, 144, 145, 148
See application file for complete search history.

(56) References Cited

U.S. PATENT DOCUMENTS

| | | |
|---|---|---|
| 987,173 A | 3/1911 | Sale |
| 5,618,290 A | 4/1997 | Toy et al. |
| 2004/0068273 A1 | 4/2004 | Fariss et al. |

(Continued)

FOREIGN PATENT DOCUMENTS

WO   97/03613 A1   2/1997

*Primary Examiner* — Katherine M Shi
(74) *Attorney, Agent, or Firm* — Baker & Hostetler LLP

(57) ABSTRACT

A tissue closure device to assist in retrieving a suture during a suturing procedure, the device including an elongated body having a proximal end, a distal end, and a lumen extending axially through the elongated body. The device further including an actuator rod at least partially extending through the lumen of the elongated body to actuate a plurality of wings and a plurality of shields attached to a distal end of the elongated body. The elongated body including at least one needle guide lumen with an opening an exit, the at least one needle guide lumen traversing the elongated body at an angle with respect to a central axis of the elongated body to guide a suture grasper to an enclosed suture retrieval cavity.

19 Claims, 8 Drawing Sheets

(56) References Cited

U.S. PATENT DOCUMENTS

| | | |
|---|---|---|
| 2006/0030868 A1 | 2/2006 | Bennett |
| 2009/0036906 A1 | 2/2009 | Stafford |
| 2010/0185217 A1 | 7/2010 | Hsu et al. |
| 2010/0280530 A1 | 11/2010 | Hashiba |
| 2012/0035623 A1 | 2/2012 | Bagaoisan et al. |
| 2012/0143221 A1 | 6/2012 | Weisel et al. |
| 2012/0296373 A1 | 11/2012 | Roorda et al. |
| 2013/0253543 A1 | 9/2013 | Heneveld |

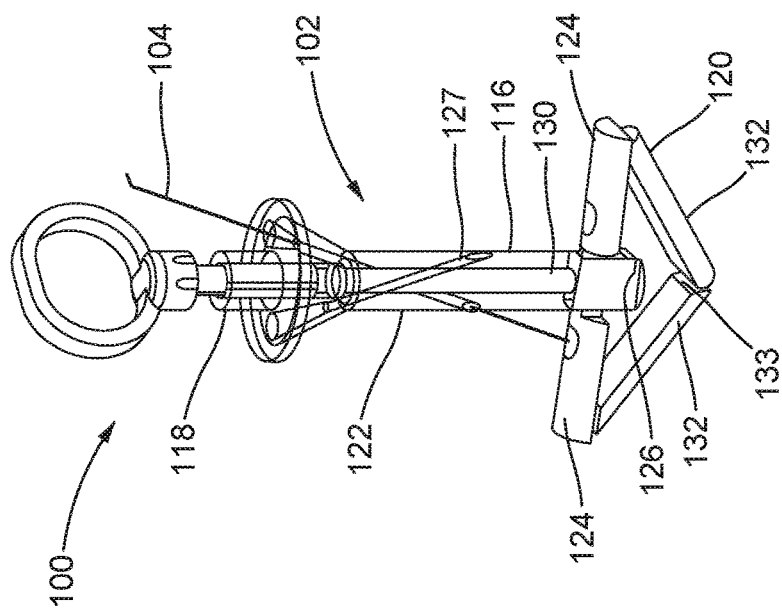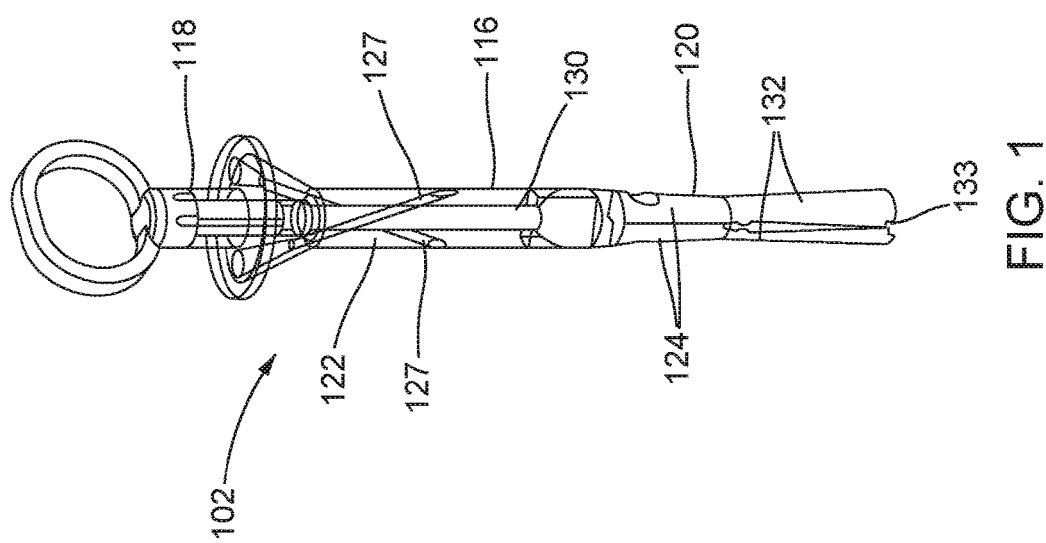

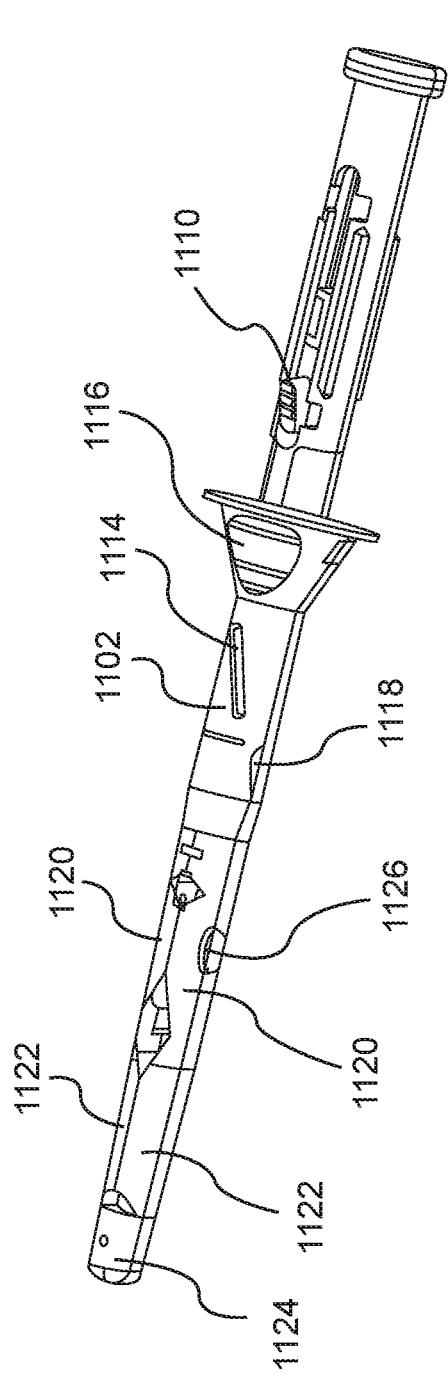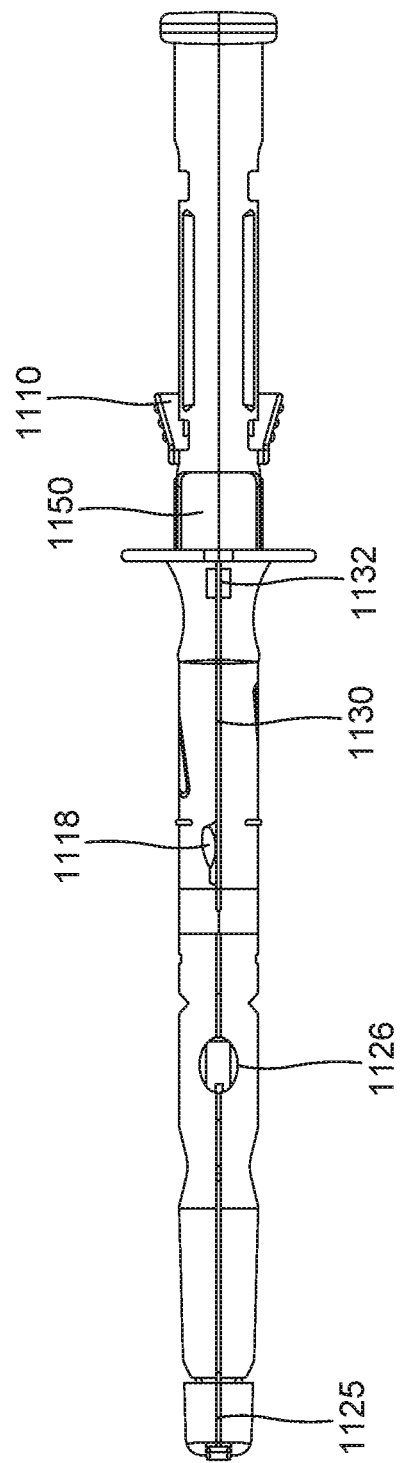
FIG. 4
FIG. 5

LAPAROSCOPIC FASCIAL CLOSURE SYSTEM

CROSS-REFERENCE TO RELATED APPLICATION

This patent application is a continuation of U.S. patent application Ser. No. 14/564,331, filed Dec. 9, 2014, which claims priority to U.S. Provisional Patent Application No. 61/913,910, filed Dec. 9, 2013, the disclosures of which are incorporated herein by reference in their entireties.

FIELD OF THE INVENTION

The present disclosure relates to tissue closure devices, and more particularly to a laparoscopic fascial closure system that includes a template and a sliding suture retrieving needle for use during an intra-abdominal suturing procedure or the suturing of a puncture wound generated by a surgical trocar or other puncturing devices.

BACKGROUND

Minimally invasive methods for conducting surgery on internal organs, tissues, ligaments and bones use extremely small instruments such as catheters, laparoscopes, and the like. The instruments are introduced using very small incisions, for example on the order of 5 mm to 18 mm in diameter, into which a trocar or other introducing device is placed. The trocars may have a diameter, for example, between 3 mm and 30 mm, with the smaller trocars leaving the opening substantially unchanged. The larger trocars may enlarge the opening. The trocars provide a reliable and fixed opening for introducing and removing various surgical instruments, viewing devices and other instruments used during the surgical procedure.

While the incisions and the trocar opening are quite small by traditional surgical standards, they still require closure after completing the surgical procedure. Surgical closure reduces the possibility of post-surgical infection, post-surgical herniation (for example in abdominal surgeries), subsequent bleeding or other effects. Closure can be accomplished either through manual suturing or suturing instruments used to complete the closure. In either case, suturing is made difficult by the small opening size, for example not only for manipulating the suture but also for visualizing the procedure. Closure is also made more difficult by the need to suture the subcutaneous tissue, for example fascial layers, separate from closure of the overlying skin, and doing so through a very small opening in the skin while also avoiding possible injury or damage to the internal organs during such a procedure.

Conventional closure techniques such as those for closing openings in the abdominal wall pass sutures through the abdominal wall tissue a distance from the original trocar incision. One or more sutures are then tied off to close the subcutaneous layer followed by suitable closure of the skin layer. It has been noted that the distance of the suture location from the original incision opening is important in order to secure a suitable amount of abdominal wall tissue for forming a reliable closure. If the distance is too small, the closure may not be enough to reliably close the opening without later complications.

Tissue closure devices, for example laparoscopic port closure devices, may be introduced into the opening after removal of the trocar device to make easier the suturing of the trocar opening. Various methods and structures may help in closing the opening, but may require a significant number of steps for completing the closure. Some devices may require a significant amount of manual care in suturing the opening and tying off the suture, as well as close visualization for accomplishing the closure. Additionally, some devices have a significant number of components or special devices in order to accomplish the closure, or they may not provide consistent and reliable results even under normal operating circumstances.

This disclosure relates to tissue closure devices, including surgical suturing devices as well as such devices that can be used for intra-abdominal suturing and suturing of puncture wounds generated by surgical trocars and other puncturing devices.

SUMMARY

A laparoscopic fascial closure system may provide a suture preloaded on a closure template for insertion into a body cavity that may be used with a suture grasper retriever to easily capture a portion of the suture with the template disposed within the body cavity and then facilitating free movement or sliding of the suture at or within the device tip during retraction of the device from the body cavity.

According to one exemplary embodiment, a tissue closure device includes an elongated body defining a central longitudinal axis and including a proximal end, a distal end, and a lumen extending axially through the elongated body. The tissue closure device further includes an actuator rod at least partially extending through the lumen of the elongated body. A distal portion of the elongated body is pivotally connected to a plurality of wings, which are pivotally connected to a plurality of shields. The plurality of shields are pivotally connected to a distal tip portion of the device, the distal tip portion being attached to a distal end of the actuator rod. The plurality of wings each include an opening to allow passage into a suture retrieval space defined between one each of the plurality of wings and plurality of shields when said wings and shield are extended away from the elongated body in a deployed position of the device.

According to one aspect, the opening is a round or open shape.

According to one aspect, each of the plurality of shields is connected to a corresponding one of the plurality of wings via living hinges.

According to one aspect, the plurality of shields and the plurality of wings are pivotally retractable to be parallel to the elongated body as the actuator rod is moved in a distal direction with respect to the elongated body.

According to one aspect, the plurality of shields and the plurality of wings extend at angles laterally away from the central longitudinal axis as the actuator rod is moved in a proximal direction with respect to the elongated body, in the deployed position.

According to one aspect, the elongated body further includes a plurality of suture runner guides to control a location of a suture loaded onto the device, each suture runner guide disposed at a predetermined position distal to an inner surface of each of the plurality of wings.

According to one aspect, the location aligns the suture in the predetermined position to allow a suture grasper to orthogonally intersect the suture, when said grasper is inserted into the suture retrieval space, after passing through the at least one needle guide lumen.

According to one aspect, the plurality of shields prevent inadvertent needle perforation of organs, vessels, or other tissues in the deployed position.

According to one aspect, a proximal portion of the elongated body includes a suture cleat for stabilizing or holding a suture taut.

According to one exemplary embodiment, a tissue closure system includes a suture grasper, a tissue closure template, the template including an elongated body defining a central longitudinal axis and having a proximal end, a distal end, a lumen extending axially through the elongated body, an actuator rod at least partially extending through the lumen of the elongated body, and at least one needle guide lumen traversing the elongated body at an angle with respect to a central axis of the elongated body. A distal portion of the elongated body is pivotally connected to a plurality of wings, which are pivotally connected to a plurality of shields, and the plurality of wings and the plurality of shields are operable to extend laterally away from the elongated body, in a deployed position, as the actuator rod is moved in a proximal direction with respect to the elongated body. The plurality of wings each include an opening to allow passage into a suture retrieval space defined between the one each of the plurality of wings and plurality of shields when extended away from the elongated body in the deployed position.

According to one aspect, a distal end of the suture grasper is insertable through the at least one needle guide lumen and through the opening of the plurality of wings while the plurality of shields are extended laterally away from the elongated body in the deployed position.

According to one aspect, the plurality of shields, in the deployed position, prevent inadvertent needle perforation of organs, vessels, or other tissues by the suture grasper as the suture grasper is inserted through the opening of the plurality of wings.

According to one aspect, the elongated body further includes a plurality of suture runner guides to control a location of a suture loaded onto the template, each suture runner guide disposed at a predetermined position distal to an inner surface of each of the plurality of wings.

According to one aspect, the location aligns the suture in the predetermined position to allow the suture grasper to orthogonally intersect the suture, when the suture grasper is inserted into the suture retrieval space.

According to one aspect, the suture grasper includes at least one element that can expand laterally to encircle the suture at the predetermined position.

BRIEF DESCRIPTION OF THE DRAWINGS

The accompanying drawings, which are incorporated in and constitute a part of this specification, illustrate various embodiments consistent with the invention, and, together with the description, serve to explain the principles of the invention.

FIG. 1 is a perspective view of a tissue closure template, in accordance with certain aspects of the present invention;

FIG. 2 is a perspective view of a fascial closure system showing a tissue closure template and a suture grasper in a certain state of use, in accordance with certain aspects of the present disclosure;

FIG. 4 is a side perspective view of a closure template, in accordance with certain aspects of the present disclosure;

FIG. 5 is a front view of a closure template, in accordance with other aspects of the present disclosure;

DETAILED DESCRIPTION

Figure 3:
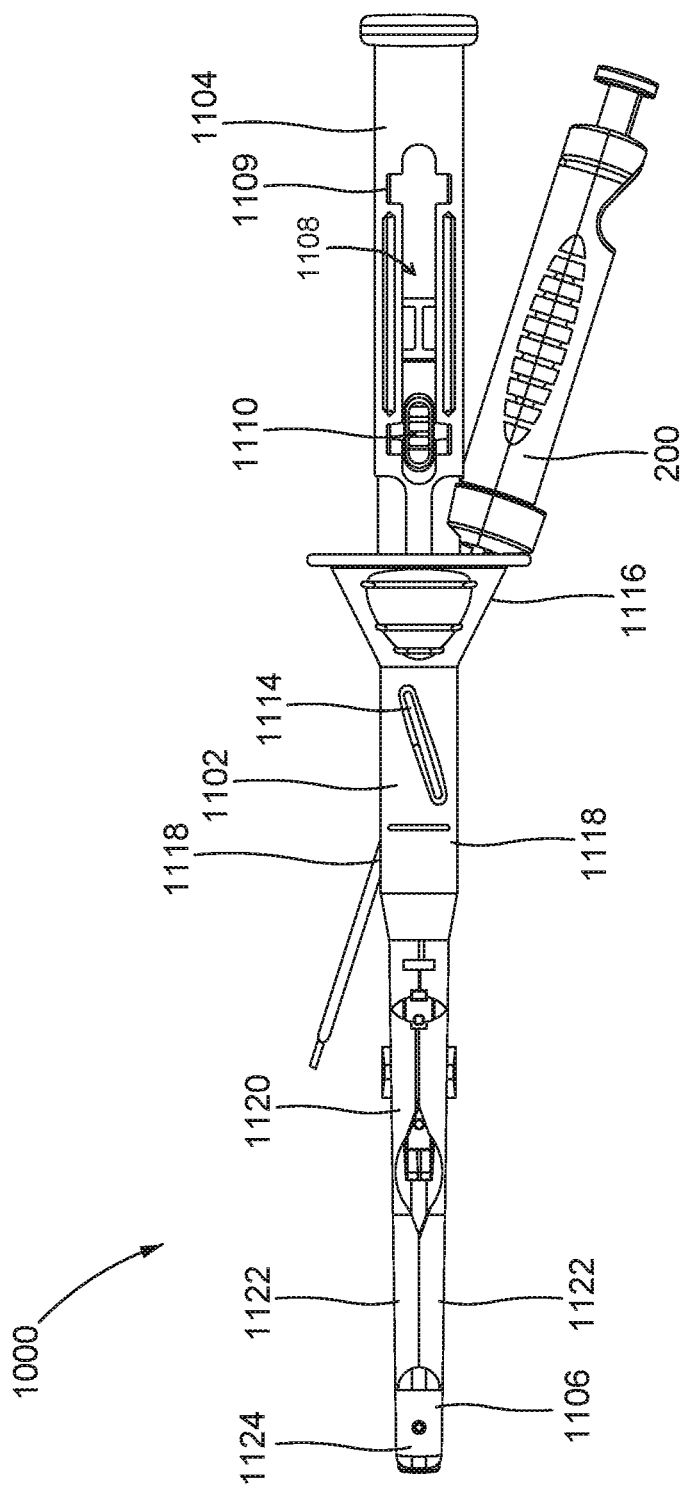
FIG. 3 is a side view of a fascial closure system, in accordance with certain aspects of the present disclosure.

The invention will now be described with reference to the drawing figures, in which like reference numerals refer to like parts throughout.

Various aspects of a laparoscopic fascial closure system may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of a laparoscopic fascial closure system or the components thereof in addition to the orientation depicted in the drawings. By way of example, if aspects of a laparoscopic fascial closure system shown in the drawings are turned over, elements described as being on the "bottom" side of the other elements would then be oriented on the "top" side of the other elements. The term "bottom" can therefore encompass both an orientation of "bottom" and "top" depending on the particular orientation of the apparatus.

Closure devices for trocar openings are used as examples of a closure device that can incorporate one or more of the features and derive some of the benefits described herein, and in particular closure devices for abdominal tissue openings. Closure of trocar openings in abdominal walls present particular issues for acceptable results, and closure devices for abdominal openings will be considered in more detail. However, closure devices other than for abdominal wound closures can benefit from one or more of the present inventions.

In accordance with one example of apparatus that can be used for closing a tissue opening, for example a trocar opening in the abdominal wall, and where the apparatus reflects one or more methods that can be used for tissue closure, a fascial closure system 100 includes a closure assembly or closure template 102 and a needle retriever 104. The closure template 102 can be used with the needle retriever 104 as discussed herein, or with other suture introducers or needles, and the needle retriever 104 as discussed herein can be used with other closure devices. However, for purposes of some of the examples, the closure device 102 and the needle assembly 104 will be considered as being used together. Additionally, the present discussion for the application of the closure assembly will be in the context of closure of an abdominal opening, but it should be understood that other tissue closures can be carried out with one or more of the components of the assembly.

In the context of a trocar opening in an abdominal wall, the opening extends through a skin and superficial layer that may include muscle, depending on the location in the abdomen at which the opening is made. The skin and superficial layer will be referred to as the skin layer for simplicity. Underlying the skin layer is a fascial layer having a thin peritoneum. The peritoneum forms the lining of the abdominal cavity outside the internal organs (not shown), and it is through the skin layer, fascial layer and peritoneum that the trocar opening and trocar permit access for an operator to the internal organs. Once the surgery is complete, the trocar opening is closed by closing the fascial layer and peritoneal layer, while taking care to avoid puncturing or injuring any underlying organs. One way to minimize puncturing underlying organs during the closure process is to retract the tissue layers away from the underlying organs and to limit or carefully control the ingress of suture introducers or retrievers beyond the tissue wall (peritoneal layer), for example in the manner described more fully below.

As shown generally in FIGS. 1 and 2, the closure template 102 in the present example includes a closure body 116. The body extends from a proximal portion 118 to a distal portion 120. Generally, the proximal portion 118 is used to control and manipulate the closure device, and the distal portion 120 forms a working structure to be inserted under the peritoneal layer. The distal portion 120 in the present examples is used to present a portion of a preloaded suture at a known and predetermined location where the suture can be reliably retrieved, for example even without visualization, and in such a way that suture bites can be made at optimal locations for forming reliable closures. For example, the distal portion 120 can be used as a target for inserting a retrieval tool through the fascial layer to the target for retrieving a pre-disposed suture portion from the target and withdrawing the suture through the fascial layer and a tissue opening to help in closing the opening.

The closure template 102 also includes an intermediate or middle portion 122, which will be generally considered that portion of the closure body 116 residing within the laparoscopic opening during normal use. The middle portion 122 generally will extend between the outer surface of the skin layer and the peritoneal layer. The middle portion 122 includes at least one element that helps to reliably and repeatably guide a needle retriever toward a predetermined target site without the operator having to substantially adjust or vary the direction of movement of the retriever. In the present examples, as discussed more fully below, the at least one element in the middle portion 122 that helps to reliably and repeatably place a suture introducer or retriever at the predetermined target site is a channel or passageway, for example a trans lateral passageway 127, through the body 116 of the closure device 102. In select aspects, the middle portion 122 may include a plurality of channels or passageways extending through the body 116 of the closure device 102.

Considering the closure template 102 in more detail, the distal portion 120 in the present example includes a plurality of wings 124, which can be planar or curved structures that span an area wider than a suture or grasper needle, up to a width of the closure body 116, 1102, in the embodiments shown in FIG. 1 or 5. The wings 124 form targets for a suture retriever 104. The wings 124 may extend outwardly in substantially opposing directions from the closure body 116 in a deployed configuration as shown in FIG. 2. They are substantially 180° apart and extend substantially perpendicular to a central axis of the closure body 116. In other examples, the closure template 102 could have a single wing or plural wings, whether arranged in pairs or otherwise. When arranged in pairs, they can be arranged in two, four, six or more pairs, as desired.

The wings 124 may be pivotally mounted to respective portions of a mounting structure 126 at the distal end of the closure body 116. The wings 124 may be linked to and operated through a pull rod 130. The pull rod 130 extends upward into and is substantially centered on the central axis of the closure body 116 for longitudinal movement within the body 116. The pull rod 130 and wings 124 are mounted to the body 116 such that upward movement of the pull rod 130 pulls the link arms or expanders upward to move the wings 124 from a collapsed or insertion configuration shown in FIG. 1 to the expanded or deployed configuration shown in FIG. 2. Downward movement of the pull rod 130 within the body 116 fold wings 124 down relative to the body into a closed configuration or geometry capable of a traumatic insertion into the body.

In addition to the wings 124 shown in FIGS. 1 and 2, the distal portion 120 may also include shield portions 132 connected to the wings 124. The shield portions 132 are also planar or curved structures which span an area wider than a suture or grasper needle, similar to the wings 124, and may be connected to the wings 124 by living hinges, for example, or by any suitable hinge structure such that actuation of the wings 124 results in a corresponding actuation of the shield portions 132. The shield portions 132 similarly extend from a closed position to an expanded or deployed position when the pull rod 130 is actuated. The shield portions 132 may also be connected at a distal end 133 and hinged to form a completely enclosed suture retrieval cavity when the wings are deployed as shown in FIG. 2. The suture retrieval cavity provides an area of protection to the surrounding tissues and/or internal organs from damage during extension of the needle retriever 104 toward the targets to retrieve a suture portion during a suture retrieval procedure.

FIG. 3 illustrates another laparoscopic fascial closure system 1000 configured in accordance with the same general concepts as outlined above. The system 1000 includes a closure template 1100 for use with a needle retriever, such as the suture grasper 200. As shown in FIGS. 3-5, the template 1100 includes an elongated body 1102 with a proximal end 1104 and a distal end 1106 and a lumen 1108 provided to extend longitudinally through the body 1102. The body 1102 may include at least one lock feature 1109 toward the proximal end that interacts with a handle 1110 connected to an actuator rod 1112. In one aspect, the handle 1110 may include portions extending laterally from the body 1102 and/or portions extending axially from the proximal end of the body 1102. At least one suture needle guide lumen 1114 may traverse a central axis at an angle from the proximal portion toward the distal portion of the body 1102. The needle guide lumen 1114 may include a funnel 1116 at the proximal end of the body 1102 to aid in the insertion of the needle and a needle guide exit lumen 1118 is located distal of the funnel 1116 and at predetermined distance away from top wings 1120. The top wings 1120 may be connected to the body 1102 via separate living hinges or a pin hinge, for example.

Figure 8:
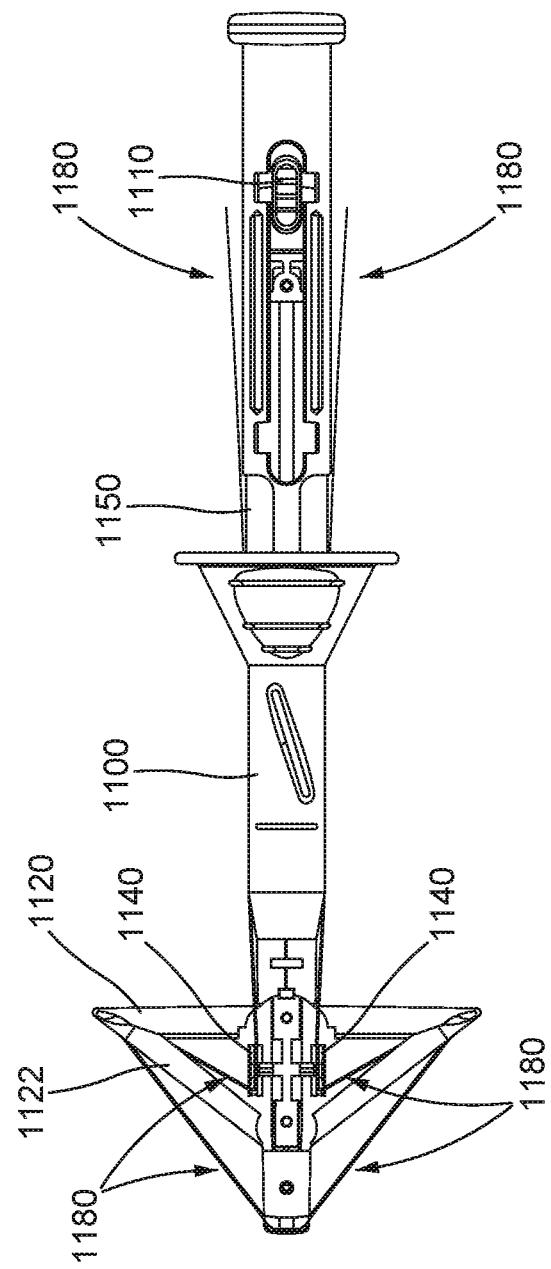
FIG. 8 is a side view of a closure template in a position of use, in accordance with certain aspects of the present disclosure.

In addition to the wings 1120, the distal portion of the template 1100 include shields 1122 pivotally connected to the wings 1120. The shield portions 1122 may be connected to the top wings 1120 by living hinges, for example, or by any suitable hinge structure. The shield portions 1122 in turn pivotally connect to a distal tip portion 1124 of the template 1100. The tip portion 1124 may be atraumatically shaped and connected to the actuator rod 1112 such that actuation of the handle 1110 results in the distal tip portion 1124 being retracted toward or extended away from the body 1102. The wings 1120 and the shield portions 1122 are thus controlled by the actuation rod 1112 to extend from a closed position to an expanded or deployed position when the actuation rod 1112 is pulled. The wings 1120 and shield portions 1122 thus form a completely enclosed suture retrieval cavity when the wings 1120 are deployed as shown in FIG. 8. The suture retrieval cavity provides an area of protection to the surrounding tissues and/or internal organs from damage during extension of the needle retriever 104 toward the targets to retrieve a suture portion during a suture retrieval procedure.

The wings 1120 may be used to locate the peritoneum and allow retraction when expanded. Each wing 1120 may include an opening 1126, which may be round or oval or any suitable shape, that allows passage of the suture grasper 200 into the suture retrieval cavity when the system is deployed. Suture positioning guides and grooves are provided in the wing and may provide a predetermined position of the suture that is designed to release away from the suture when the wings are collapsed and the template is retracted out of the body cavity.

Suture retaining means such as living hinge clamp and the like (not shown) may be integrated and located at the proximal portion of the body that may be used as an alternative design to the cleat described below. Suture clamps temporarily hold the suture in place when loaded in the device and may allow the suture to slide or move when the wings are activated from a collapse to an open position.

Suture positioning guides or grooves 1130 may also be provided along the length of the body in order to load and place a portion of a suture strand at a predetermined position relative to the lateral wing in the open or deployed position. The guides and grooves serve to hide the suture by positioning it below the outer surface of the device when suture is loaded, which may prevent inadvertent suture dislodgement during insertion of device to the patient.

An active or passive clamping or cleating means of holding the suture in place after loading the suture to the device may be used. For example, a suture cleat 1132 may be located toward the proximal portion of the body to hold the suture taut or stabilize the suture when loaded in the device during insertion, wing expansion and suture retrieval. The clamp or cleat 1132 may allow the suture to slide or move when the lateral wings 1120 are opened and/or during suture pick-up and withdrawal using a suture grasper and the like.

The body 1102 may include a keyway on the proximal end of the template that interacts with a key feature on the proximal handle of the suture grasper device 200. The key and keyway could be configured such that the lateral expanding element is generally orthogonal to the suture to be captured held in the template when the key resides in the keyway. The key/keyway feature could act as a stop and limit the penetration distance of the needle. The user could be instructed to bottom out the handle of the retriever directly against the insertion point for the retriever on the template.

The shield portions 1122 are located toward the distal portion of the template. As noted above, the shield portions 1122 may prevent inadvertent needle perforation of organs or vessels or other tissues and may serve as column support for the lateral wings 1120. The shield portions 1122 may comprise at least one hinge connecting the distal shield and the top wing. The hinge configuration may comprise a pin or living hinge or combination thereof. A living hinge may be configured to have constant thickness at predefined length that forms a radius transition between the top wing 1120 and the shield portion 1122. A larger radius transition will bring the (inner surface of) the shield farther away from the top wing when in the open position. This in turn increases the working space where the suture can be positioned and make room for the suture grasper 200 when capturing the suture.

As shown in FIG. 5, a suture guide slot 1125 may be provided at the distal tip 1124 that keeps the suture in place. The slot 1125 provides a predetermined position of the suture and is designed to release away from the suture when the template is retracted out of the body.

Figure 6:
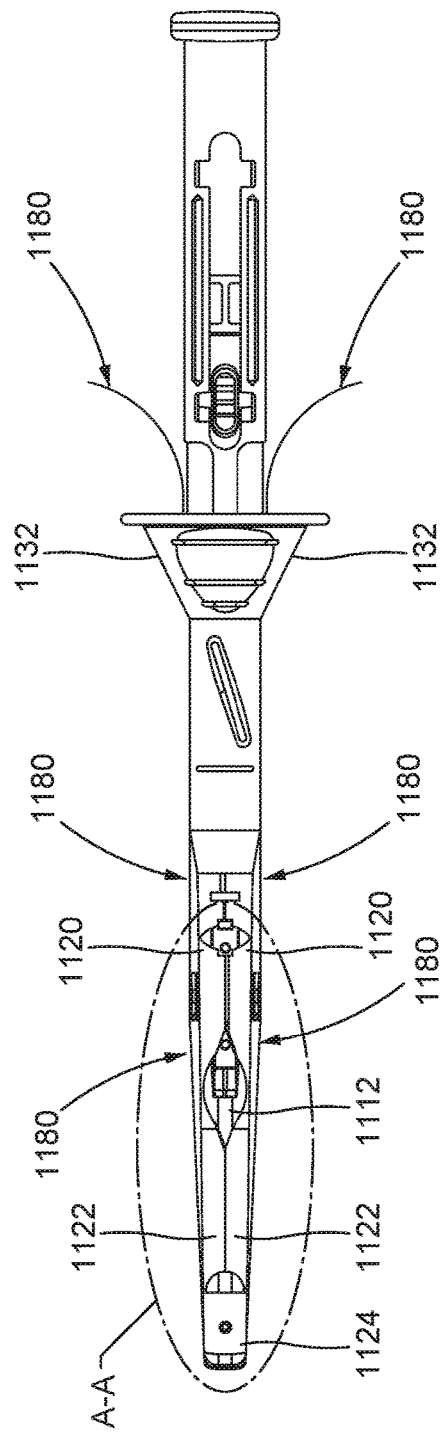
FIG. 6 is a side view of a closure template, in accordance with certain aspects of the present disclosure.
Figure 7:
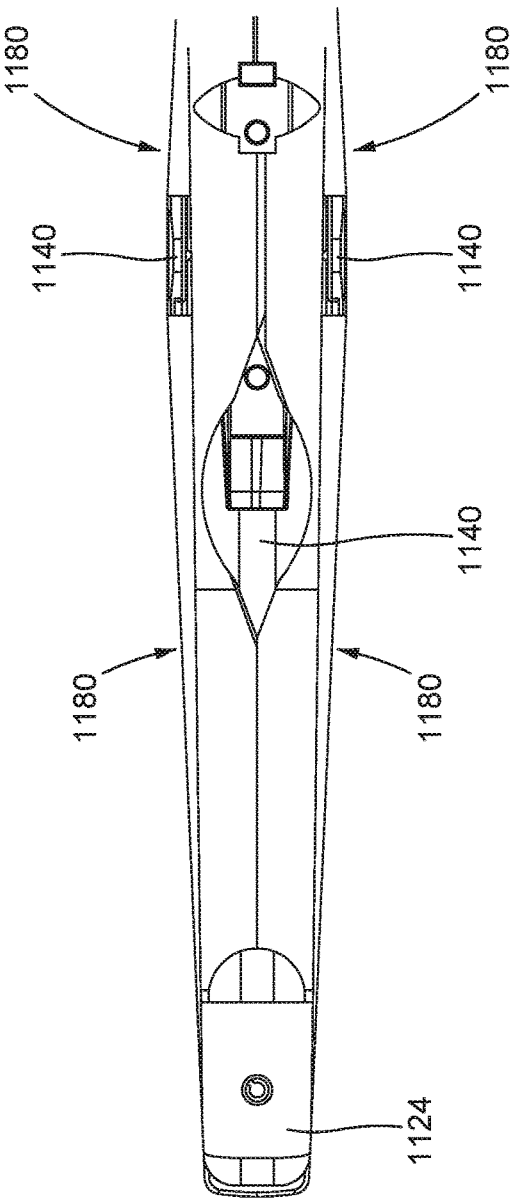
FIG. 7 is an enlarged side view of a distal portion of a closure template of FIG. 6 at A-A.
Figure 9:
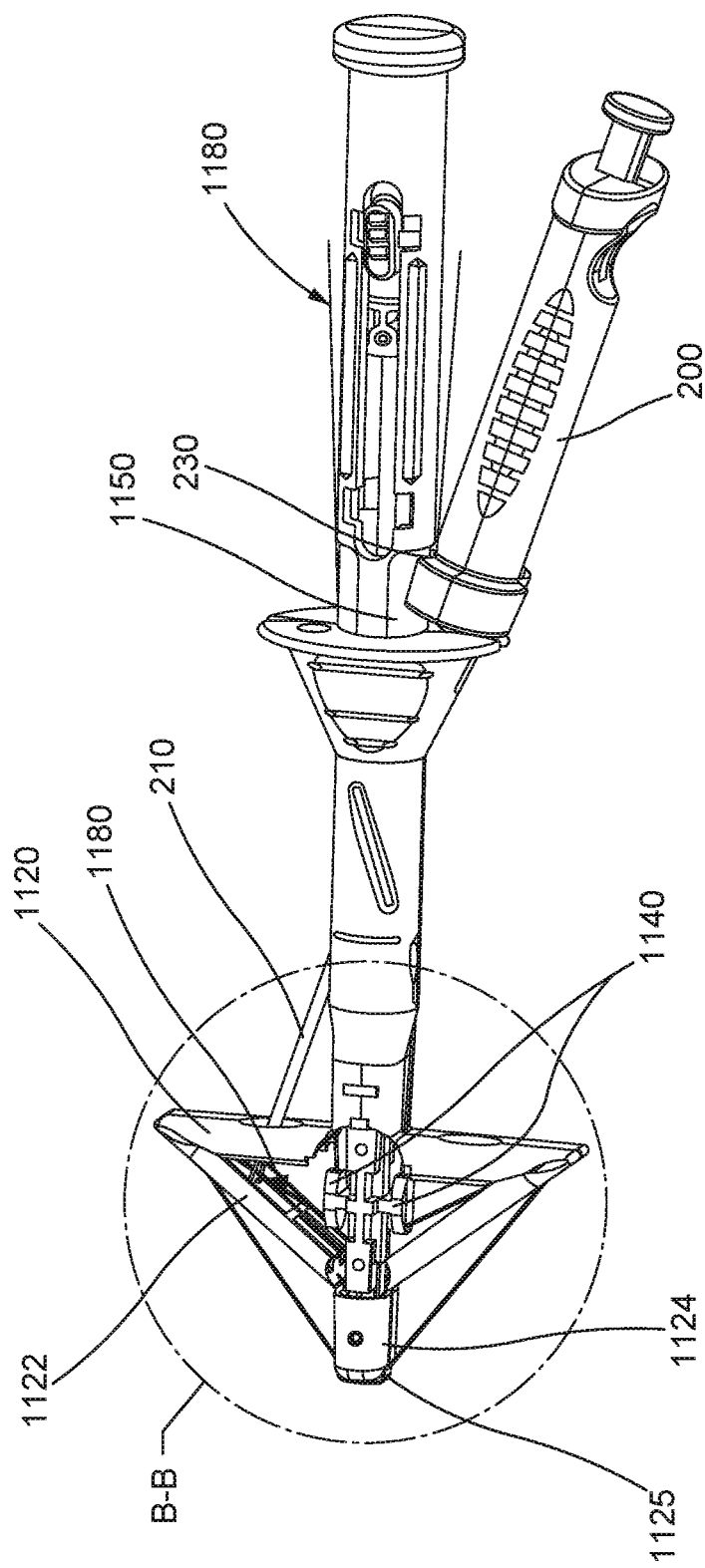
FIG. 9 is a side perspective view of a closure template in a position of use, in accordance with certain aspects of the present disclosure.
Figure 10:
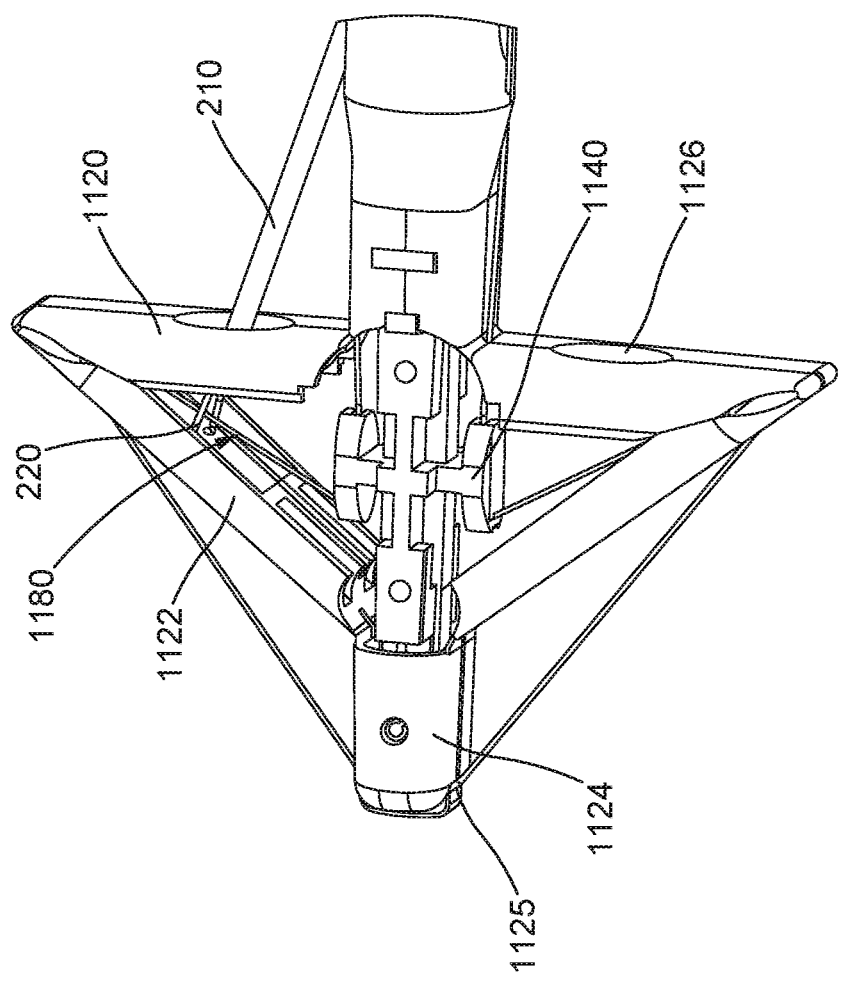
FIG. 10 is an enlarged side view of a distal portion of a closure template of FIG. 9 at B-B.

As shown in FIGS. 6 and 7, the actuator rod 1112 may be arranged slidably along the body of the template connecting the distal tip portion 1124 of the device and the proximal handle 1110. When the driver is retracted proximally, the wings 1120 change from a collapsed profile to the expanded lateral position, as shown in FIGS. 8-10. The driver and/or handle 1110 can be spring loaded at the proximal end the body to bias the driver 1110 either proximally to maintain the close profile or distally to maintain the expanded lateral position. An operator would overcome the spring force to either open or close the wing depending upon the spring configuration chosen.

The side loading suture slot 1130 retains the suture 1180 during insertion and is configured to allow release of the suture during retraction of the suture retriever. A suture runner guide 1140 (see also FIGS. 9 and 10) is provided on the body that controls the location of the suture at a predetermined position below the inner surface of the top wing 1122 when the top wings are opened lateral to the body. The location is configured to allow the intersection of the suture grasper 200 to the suture to be aligned generally orthogonal to each other.

Figure 11:
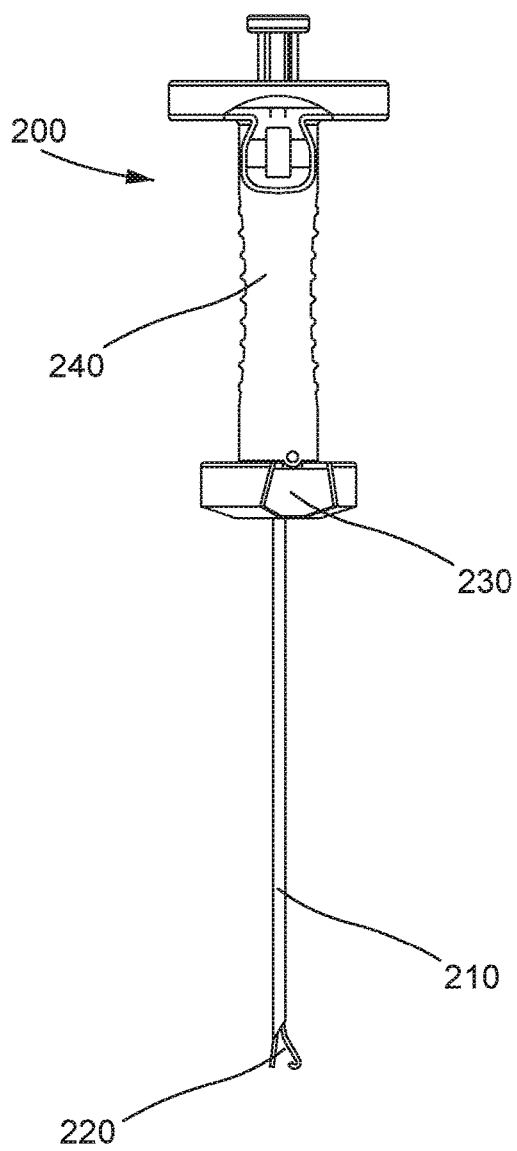
FIG. 11 is a front view of a suture grasper, in accordance with certain aspects of the present disclosure in a certain state of use.
Figure 12:
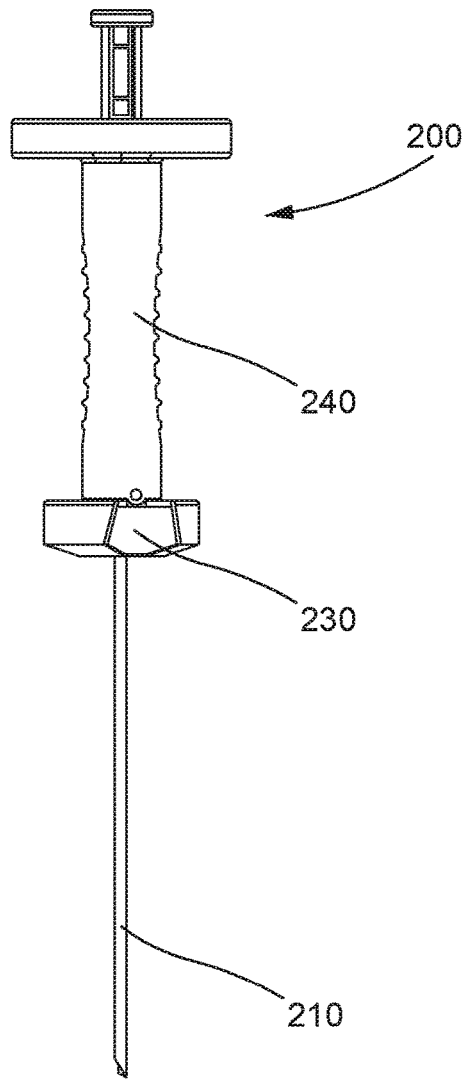
FIG. 12 is a rear view of a suture grasper in accordance with certain aspects of the present invention.

As shown in FIGS. 11 and 12, the suture grasper 200 may be a needle 210 combined with a means to retrieve suture from the template. In one aspect, the means to retrieve suture from the template may include at least one grasping element 220.

The suture grasper 200 may be inserted into an insertion point on the proximal portion of the template body 1102 transverse to the centerline of the template through an exit point of the template body 1102 through the soft tissue and across the aperture opening of the top wing in proximity of the suture to allow its capture and retrieval. This retrieval maneuver could then be repeated on the opposite side of the template to facilitate retrieval of the suture there.

The suture grasper 200 may include at least one element 220 that can expand laterally to encircle the suture 1180 and is configured to allow the suture 1180 to slide freely after the suture has been captured. The suture grasper 200 may include a key feature 230 on the proximal handle 240 that interacts with a keyway 1150 on the proximal end of the template, as shown in FIGS. 3 and 9. In one aspect, the key feature 230 may be a planar surface tapering inwards towards the needle 210, while the keyway 1150 may be a planar surface extending in parallel with the central axis of the closure body 116. In operation, the planar surface of the key 230 may abut the planar surface of the keyway 1150 to align the lateral expanding element 220 with respect to the suture. The key 230 and keyway 1150 could be configured such that the lateral expanding element 220 is generally orthogonal to the suture 1180 to be captured held in the template when the key 230 resides in the keyway 1150. The key/keyway feature could act as a stop and limit the penetration distance of the needle 210. The user could be instructed to bottom out the handle 240 of the retriever directly against the insertion point for the retriever on the template.

The suture grasper 200 may be configured to automatically activate to expand when approaching the suture target and to deactivate or close when retracting the retriever thereby capturing the suture during the retraction maneuver. This would allow a surgeon to engage and remove suture using a blind technique without visualization. The activation/deactivation feature could work in conjunction with the key/keyway arrangement mentioned previously.

The suture 1180 is loaded on the outside perimeter of the device with the wings 1120 in a collapsed state, as shown in FIGS. 6 and 7, for example, wherein the mid portion of the suture 1180 is mounted to the suture slot 1125 at the distal tip 1124 of the device, then runs under a slot of the suture runner guides 1140 on the distal end of the body and then continuously runs alongside the body of the device. The suture 1180 is pulled taut and secured by the clamp or cleat 1132 located at the proximal portion of the device. The template 1100 may be inserted through a hole into the body cavity. The wings 1120 are actuated to expand open and the device is retracted to engage the top wing 1120 against the peritoneum. The suture grasper 200 may be inserted through the body of the template 1100, traversing the soft tissue and crossing the aperture 1126 of the top wing to engage and capture the suture positioned in the suture retrieval cavity. The grasper 200 is retracted out of the body cavity with the suture 1180 sliding freely at its distal tip to externalize the terminal end of the suture. The steps are repeated on the other side of the template 1100 and then the wings 1120 of the device are deactivated or closed, thereby releasing the suture 1180 and then the device is retracted and removed from the body cavity. A knot is tied using the exposed ends of the suture to close the fascia.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

What is claimed is:

1. A tissue closure device comprising:
an elongated body defining a central longitudinal axis and including a proximal end, a distal end, and at least one guide lumen with an opening and an exit, the at least one guide lumen traversing the elongated body at an angle with respect to the central longitudinal axis of the elongated body;
a plurality of wings pivotally connected to a distal portion of the elongated body; and
a plurality of shields pivotally connected to the plurality of wings,
wherein the plurality of wings each include an opening to allow passage of a suture grasper into a suture retrieval space defined between one each of the plurality of wings and plurality of shields when said wings and shield are extended away from the elongated body in a deployed position, and the plurality of shields prevent inadvertent perforation of organs, vessels, or other tissues in the deployed position by the suture grasper as the suture grasper is inserted through the opening of the plurality of wings.

2. The tissue closure device of claim 1, wherein the opening is round or oval shaped.

3. The tissue closure device of claim 1, wherein each of the plurality of shields is connected to a corresponding one of the plurality of wings via a living hinge.

4. The tissue closure device of claim 1, wherein the plurality of shields and the plurality of wings are pivotally retractable to be parallel to the elongated body as the tissue closure device is moved from the deployed position to a collapsed position.

5. The tissue closure device of claim 4, wherein the plurality of shields and the plurality of wings extend at angles laterally away from the central longitudinal axis when the tissue closure device is in the deployed position.

6. The tissue closure device of claim 1, wherein the elongated body further includes a plurality of suture runner guides to control a location of a suture loaded onto the tissue closure device, and each suture runner guide is disposed distal of an inner surface of each of the plurality of wings.

7. The tissue closure device of claim 6, wherein each of the suture runner guides aligns the suture to allow the suture grasper to orthogonally intersect the suture when said suture grasper is inserted into the suture retrieval space and after passing through the at least one guide lumen.

8. The tissue closure device of claim 1, wherein a proximal portion of the elongated body includes a suture cleat for stabilizing or holding a suture taut.

9. The tissue closure device of claim 1, further comprising a suture, wherein a portion of the suture is received in the suture retrieval space, and the opening allows passage of the suture grasper into the suture retrieval space to engage the portion of the suture.

10. A tissue closure system for a suturing procedure, the tissue closure device system comprising:
a suture grasper; and
a tissue closure template, the tissue closure template including:
an elongated body defining a central longitudinal axis and having a proximal end, a distal end, and at least one guide lumen with an opening and an exit, the at least one guide lumen traversing the elongated body at an angle with respect to the central longitudinal axis of the elongated body,
wherein a distal portion of the elongated body is pivotally connected to a plurality of wings, the plurality of wings are pivotally connected to a plurality of shields, and the plurality of wings and the plurality of shields are operable to extend laterally away from the elongated body in a deployed position, and wherein the plurality of wings each include an opening to allow passage of the suture grasper into a suture retrieval space defined between the one each of the plurality of wings and plurality of shields when extended away from the elongated body in the deployed position, and the plurality of shields prevent inadvertent perforation of organs, vessels, or other tissues in the deployed position by the suture grasper as the suture grasper is inserted through the opening of the plurality of wings.

11. The tissue closure system of claim 10, wherein a distal end of the suture grasper is insertable through the at least one guide lumen and through the opening of the plurality of wings while the plurality of shields are extended laterally away from the elongated body in the deployed position.

12. The tissue closure system of claim 10, wherein the elongated body further includes a plurality of suture runner guides to control a location of a suture loaded onto the tissue closure template, each suture runner guide disposed distal of an inner surface of each of the plurality of wings.

13. The tissue closure system of claim 12, wherein each suture runner guide aligns the suture to allow the suture grasper to orthogonally intersect the suture when the suture grasper is inserted into the suture retrieval space.

14. The tissue closure system of claim 13, wherein the suture grasper includes at least one element configured to expand laterally to encircle the suture.

15. The tissue closure system of claim 10, further comprising a suture, wherein a portion of the suture is received in the suture retrieval space, and the opening allows passage of the suture grasper into the suture retrieval space to engage the portion of the suture.

16. A tissue closure system for a suturing procedure, the tissue closure system comprising:
   a suture grasper; and
   a tissue closure template, the tissue closure template including:
   an elongated body defining a central longitudinal axis and having a proximal end, a distal end, and at least one guide lumen with an opening and an exit, the at least one guide lumen traversing the elongated body at an angle with respect to the central longitudinal axis of the elongated body, and
   a plurality of suture runner guides to control a location of a suture, each suture runner guide disposed distal of an inner surface of each of the plurality of wings,
   wherein a distal portion of the elongated body is pivotally connected to a plurality of wings, the plurality of wings are pivotally connected to a plurality of shields, and the plurality of wings and the plurality of shields are operable to extend laterally away from the elongated body in a deployed position, and
   wherein the plurality of wings each include an opening to allow passage of the suture grasper into a suture retrieval space defined between the one each of the plurality of wings and plurality of shields when extended away from the elongated body in the deployed position.

17. The tissue closure system of claim 16, wherein each suture runner guide aligns the suture to allow the suture grasper to orthogonally intersect the suture when the suture grasper is inserted into the suture retrieval space.

18. The tissue closure system of claim 17, wherein the suture grasper includes at least one element configured to expand laterally to encircle the suture.

19. The tissue closure device of claim 16, further comprising a suture, wherein a portion of the suture is received in the suture retrieval space, and the opening allows passage of the suture grasper into the suture retrieval space to engage the portion of the suture.

* * * * *